United States Patent [19]

Watanabe et al.

[11] 4,191,194
[45] Mar. 4, 1980

[54] BLOOD VESSEL TESTER

[76] Inventors: Toshio Watanabe, 1-28, Shirasagi 1-chome, Nakano-ku, Tokyo; Yoshinori Tanimoto, 6, Kawada-cho, Shinju-ku, Tokyo, both of Japan

[21] Appl. No.: 876,138

[22] Filed: Feb. 8, 1978

[30] Foreign Application Priority Data

Feb. 14, 1977 [JP] Japan .................................. 52-14718

[51] Int. Cl.² ............................................... A61B 5/02
[52] U.S. Cl. .................................................... 128/692
[58] Field of Search .......... 128/2 H, 2.05 F, 691–694, 128/736; 73/204, 349

[56] References Cited

U.S. PATENT DOCUMENTS

| 1,622,887 | 3/1927 | Smith | 128/2 H |
| 3,595,079 | 7/1971 | Grahn | 128/2.05 F |
| 3,719,071 | 3/1973 | Hohenberg | 73/349 |
| 3,968,689 | 7/1976 | Leshner | 73/349 |
| 4,004,576 | 1/1977 | Gähwiler | 128/2.05 F |

FOREIGN PATENT DOCUMENTS

| 932977 | 9/1973 | Canada | 128/2.05 F |
| 1469132 | 1/1967 | France | 128/419 PS |
| 1294612 | 11/1972 | United Kingdom | 128/2.05 F |

OTHER PUBLICATIONS

Olmsted, F., *Measurement of Cardiac Output in Unrestrained Dogs by an Implanted Electromagnetic Meter*, IEEE Trans., Dec. 1959, pp. 210–213.

*Primary Examiner*—Robert W. Michell
*Assistant Examiner*—Francis J. Jaworski
*Attorney, Agent, or Firm*—Blanchard, Flynn, Thiel, Boutell & Tanis

[57] ABSTRACT

A blood vessel tester having two thermocouples and a measuring instrument, the junctions of the thermocouples being adapted to contact the surface of a blood vessel to be tested so that they may be positioned spaced from each other a predetermined distance, whereby when a cooling liquid is transfused into the blood vessel the change of the thermoelectromotive forces of the thermocouples with time is measured thereby to determine the degree of clearness of the blood vessel and the blood flow therein.

4 Claims, 5 Drawing Figures

BLOOD VESSEL TESTER

BACKGROUND OF THE INVENTION

The present invention relates to a blood-vessel tester for inspecting the degree of clearness or unobstructedness inside a blood vessel as well as the blood flow therein.

After an operation for vascular transplantation has been performed on a human body, it is a common practice to inspect to determine whether or not the sutured parts of the operated blood vessels are uncontracted and whether or not the above blood vessels are unobstructed, so as to learn whether or not the postoperative course is uneventful.

If, for instance, there is any contraction or obstruction in the coronary artery, angina pectoris or myocardial infarction will occur. In one of the methods of treating such a disease, an operation is performed which connects a bypass blood vessel at one end thereof to the coronary artery and at the other end thereof to the aorta by anastomosis so that the bypass blood vessel may share the blood flow with the coronary artery. In this case, the postoperative condition of the patient depends mainly upon the degree of clearness inside the bypass blood vessel and the blood flow rate therein; therefore, it is indispensable for such an operation as above to inspect the degree of clearness inside the bypass blood vessel and the blood flow rate therein. The method heretofore adopted for this purpose is to insert a catheter into a peripheral artery either exposed or tapped through the skin under a locally anesthetized condition and then to introduce the catheter into the bypass blood vessel while transfusing a contrast medium into the blood for X-ray photography. This method is reliable in that it can directly observe the condition of blood flow; however, it has disadvantages in that it is low in sensitivity with respect to the degree of clearness inside the blood vessel and to the blood flow rate, it requires complicated techniques for operation, it cannot be performed without risk, it cannot be performed repeatedly because it gives mental and physical pain to the patient, and it requires great expense.

BRIEF SUMMARY OF THE INVENTION

Therefore, it is an object of the present invention to provide a blood vessel tester which can inspect the degree of clearness inside a blood vessel and the blood flow therein very safely and accurately.

It is another object of the present invention to provide a blood vessel tester which can inspect the degree of clearness inside a blood vessel and the blood flow therein repeatedly without giving mental and physical pain to the patient.

It is still another object of the present invention to provide a blood vessel tester which can be operated very easily and inexpensively.

According to the present invention, two sets of thermocouples are connected, each at one junction, to two points on the surface of a blood vessel which points are properly spaced from each other, respectively, while their other junctions are kept at a predetermined temperature; and means are provided to detect the change of the thermoelectromotive forces of the respective thermocouples with time occurring when a cooling liquid is transfused into the blood vessel, so as to determine the degree of clearness inside the blood vessel and the blood flow rate therein.

DETAILED DESCRIPTION OF THE PREFERRED EMBODIMENTS

The present invention will be hereinafter described in detail with reference to the accompanying drawings.

Figure 1:
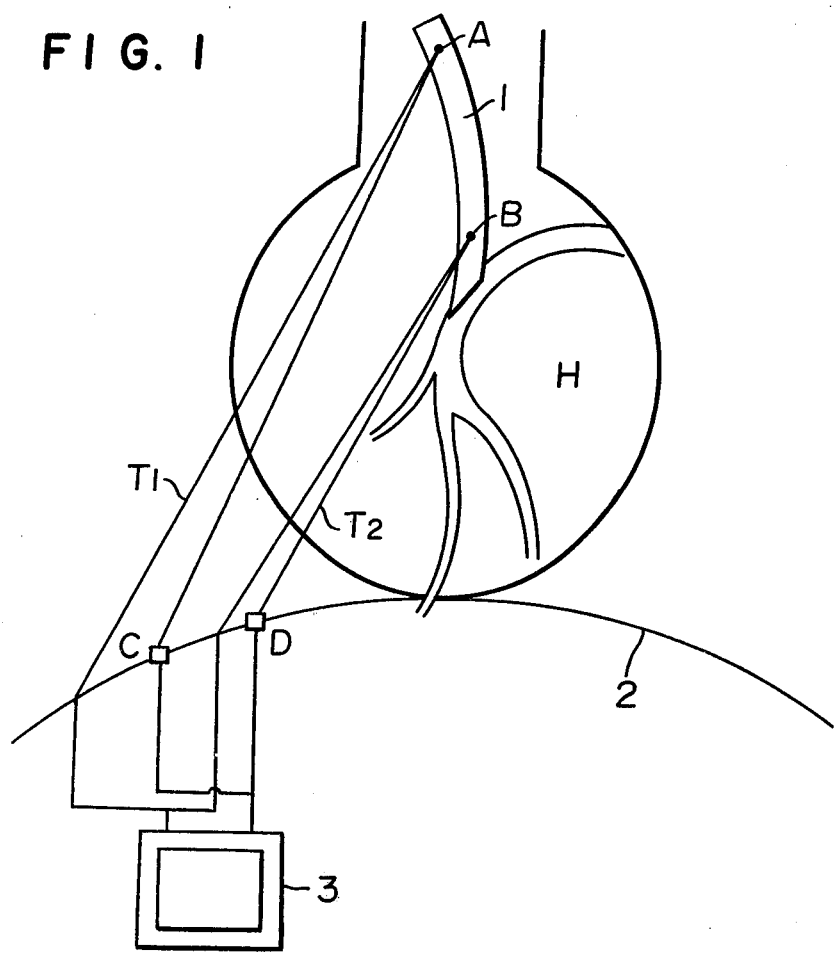
FIG. 1 is a schematic drawing showing how the degree of clearness of a blood vessel and the blood flow therein are detected by use of a blood vessel tester according to one preferred embodiment of the present invention.

Reference is first made to FIG. 1. Reference character H designates the heart, and reference numerals 1 and 2 designate a transplanted bypass blood vessel and the diaphragm, respectively. Reference character $T_1$ designates a first thermocouple, and $T_2$ designates a second thermocouple. In the present invention, commonly-used thermocouples may be used, such as those of gold-silver, platinum—German silver, gold—German silver, platinum rhodium (60% platinum, 40% rhodium)—platinum rhodium (80% platinum, 20% rhodium), and iron-constantan.

It is necessary that the portions of the metal wires of the thermocouples with which the human body is or may come in contact should be coated with a proper material of low toxicity to living bodies, such as high molecular compounds and silicone.

Reference characters A and B designate junctions of the thermocouples $T_1$ and $T_2$, respectively. The junctions A and B are brought into contact with the outside or inside surface of the bypass blood vessel 1 by sewing, adhesion or butting, and they are positioned spaced from each other a predetermined distance.

Reference characters C designate the terminals of the thermocouple $T_1$, which terminals are placed in contact with the diaphragm 2 by sewing or butting and these terminals are connected to a potentiometer 3. Reference characters D designate the terminals of the thermocouple $T_2$, which terminals are placed in contact with the diaphragm 2 by sewing or butting and are connected to the potentiometer 3 like the terminals junctions C. Thus these terminals C and D' are kept substantially at the body temperature.

Figure 2:
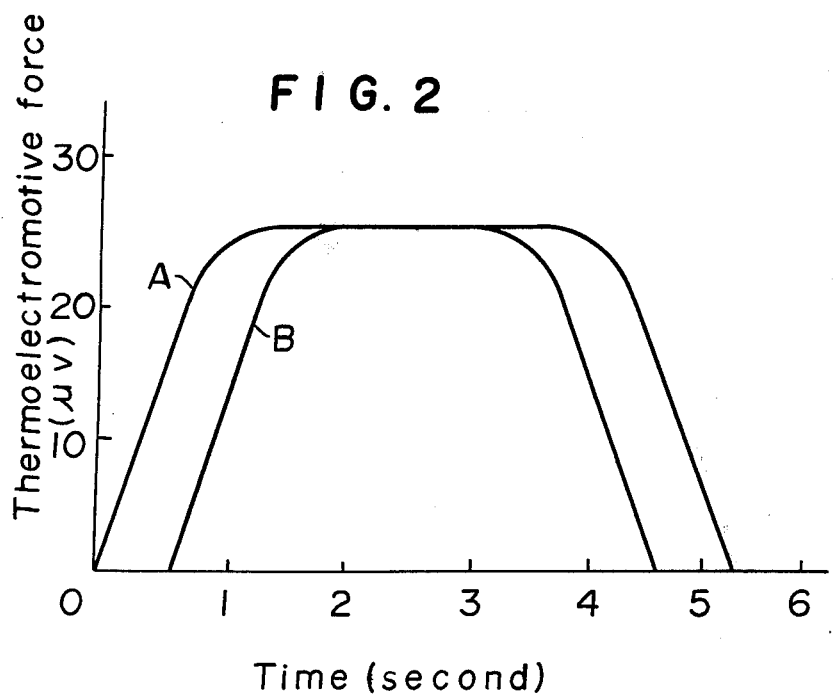
FIG. 2 is a graph showing the change of the thermoelectromotive forces of two thermocouples with time occurring when a cooling liquid is transfused into the blood vessel shown in FIG. 1 from point A toward point B, the above two thermocouples being connected to points A and B as shown, respectively.

The temperature difference between the junction A and terminals C and that between the junction B and terminals D are usually very small and can hardly be detected by potentiometers. If, however, a cooling liquid is transfused into the blood through a peripheral artery, the thus cooled blood will flow into the bypass blood vessel 1 through the right atrium, right ventricle, lungs, left ventricle and aorta. Thus the junction A is first cooled and thereby the temperature difference between the junction A and terminals C is increased and, as a result, a thermoelectromotive force is created therebetween. As the cooling liquid passes across the junction A, the above-mentioned thermoelectromotive force gradually increases and then decreases as shown in FIG. 2, which shows a curve of the change of the thermoelectromotive force with time. After passing the junction A, the cooling liquid passes the junction B thereby cooling the junction B in the same manner as in the case of the junction A. Thus the temperature difference between the junction B and terminals D is increased and, as a result, a thermoelectromotive force is created therebetween. As the cooling liquid passes the junction B, the above-mentioned thermoelectromotive force gradually increases and then decreases in the same manner as in the case of the junction A. Thus the curve of the change of the thermoelectromotive force with time in this case is substantially similar in phase to that in the case of the junction A, as shown in FIG. 2. The period of time T required for the cooling liquid to pass through the distance between the junctions A and B may be obtained from the time difference between the corresponding points of the above two curves.

In this case, the blood flow rate in the blood vessel can be obtained from the following expression:

$$\text{Blood flow rate} = \pi r^2 l/T/\text{sec} \\ = 60\ \pi r^2 l/T/\text{min}$$

where $l$ is the distance between the junctions A and B, T the period of time required for the cooling liquid to pass through the distance between junctions A and B, and r the inside diameter of the blood vessel.

The degree of clearness or unobstructedness of the blood vessel and the quality of operation can be judged from the blood flow rate thus obtained.

Figure 3:
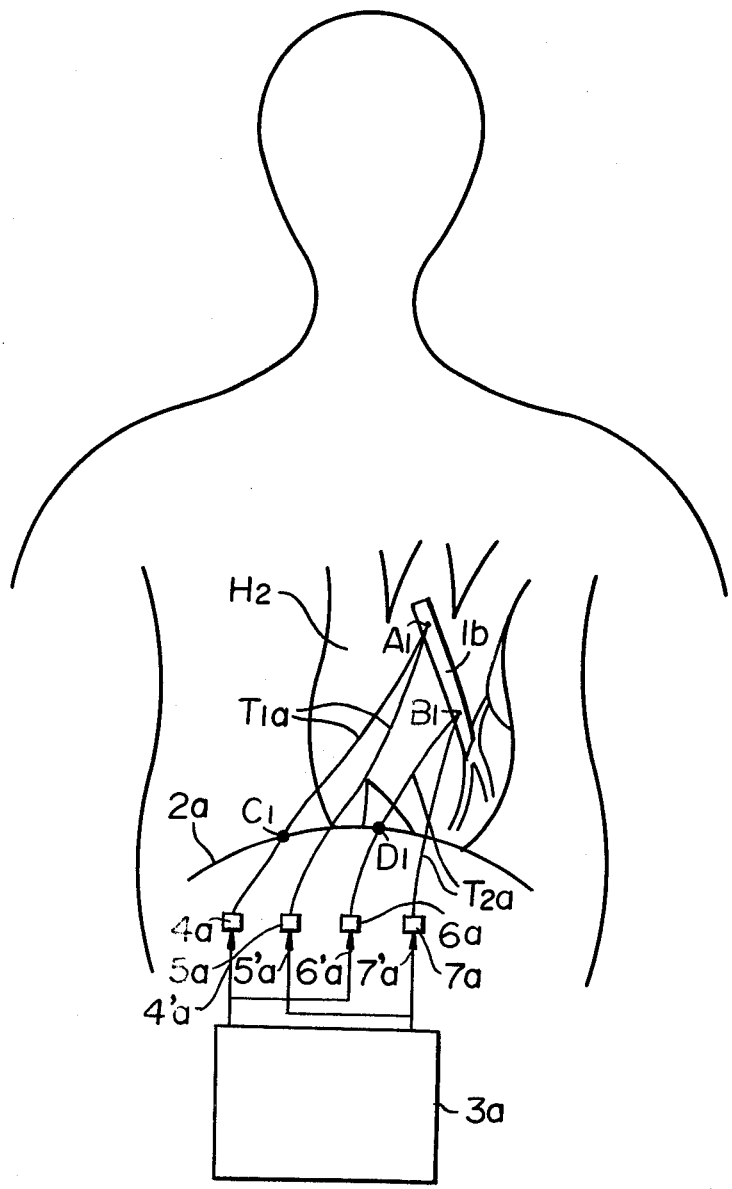
FIGS. 3 and 4 are schematic drawings showing how the degree of clearness of a blood vessel and the blood flow therein are detected by the use of a blood vessel tester according to another preferred embodiment of the present invention.

Another preferred embodiment of the present invention will be hereinafter described with reference to FIG. 3.

Reference character $H_2$ designates the heart. Reference numeral $1b$ designates a bypass blood vessel provided by an operation. Reference characters $T_{1a}$ and $T_{2a}$ designate thermocouples, respectively. $A_1$ and $B_1$ designate the junctions of the thermocouples $T_{1a}$ and $T_{2a}$, respectively. The junctions $A_1$ and $B_1$ are placed in contact with the surface of the blood vessel $1b$, being positioned properly spaced from each other. Reference characters $C_1$ and $D_1$ designate other terminals of the thermocouples $T_{1a}$ and $T_{2a}$, which terminals are placed in contact with the diaphragm $2a$. Reference numerals $4a$ and $5a$ designate terminal plates provided at the ends of the thermocouple $T_{1a}$. Reference numerals $6a$ and $7a$ designate terminal plates provided at the ends of the thermocouple $T_{2a}$. The above terminal plates $4a$, $5a$, $6a$ and $7a$ are coated with material of low toxicity to living bodies such as high molecular compounds and silicone, being embedded beneath the skin of a patient. Reference numeral $3a$ designates a measuring instrument such as a potentiometer with or without an automatic recording function.

Reference numerals $4'a$, $5'a$, $6'a$ and $7'a$ designate metal needles connected to the measuring instrument $3a$, respectively. These needles $4'a$, $5'a$, $6'a$ and $7'a$ are inserted in the skin, being electrically connected to the terminal plates $4a$, $5a$, $6a$ and $7a$, respectively. In this embodiment, the clearness of the operated blood vessel and the quality of operation can be obtained substantially in the same manner as in the case of the first embodiment.

According to this embodiment, inspection of the blood vessel can be performed accurately and rapidly without giving much pain to the patient, because the metal needles can be brought into contact with the terminal plates very easily by externally inserting the metal needles into the skin of the patient.

Figure 4:
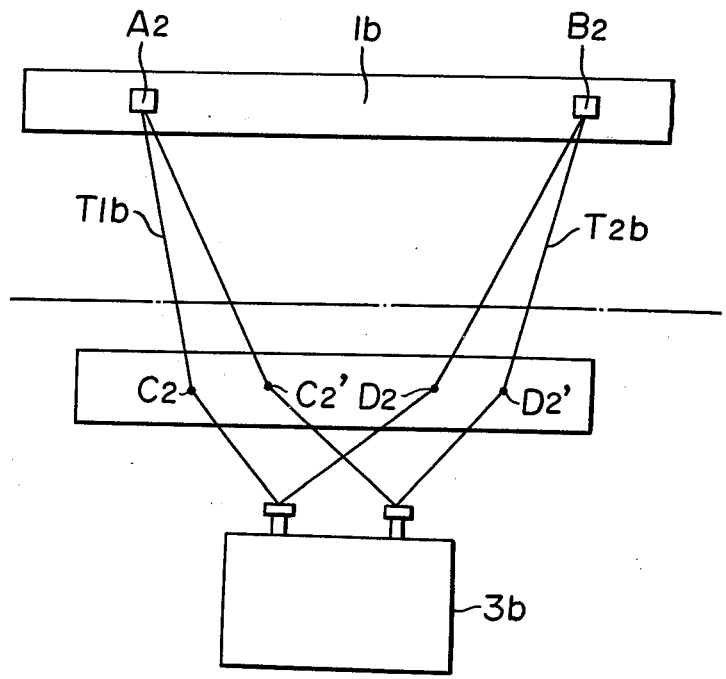

Further another embodiment of the present invention will be hereinafter described with reference to FIG. 4.

Reference character $A_2$ and $B_2$ designate the junctions of the thermocouples $T_1b$ and $T_2b$ respectively. Reference character $C_2$ and $C_2'$ designate other terminals of the thermocouple $T_1b$ which are positioned out of the patients body and are kept at a definite temperature.

Reference character $D_2$ and $D_2'$ also designate other terminals of the thermocouple $T_2b$ which are kept at a definite temperature out of the patient's body as in $C_2$ and $C_2'$. The terminals $C_2$, $C_2'$, $D_2$ and $D_2'$ are connected to the measuring instrument $3b$ with metal wires.

When a cooling liquid is transfused into the bypass blood vessel $1b$ through a peripheral artery, a thermoelectromotive force is created between the junction $A_2$ and terminals $C_2'$ and whereby it is indicated on the measuring instrument $3b$. As the cooling liquid passes through $A_2$ to $B_2$, a thermoelectromotive force is created with the thermocouple $T_2b$ whereby it is indicated on the measuring instrument $3b$. Then, according to the same procedure as that described in the foregoing, the degree of clearness inside the blood vessel and the blood flow rate therein may be determined.

Figure 5:
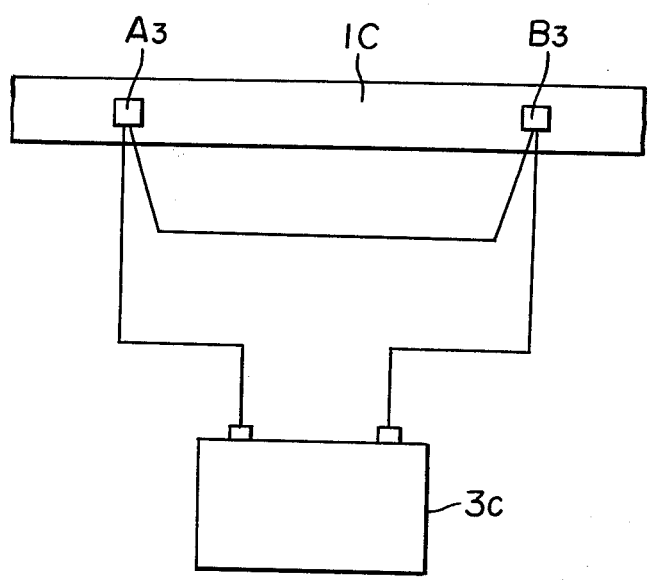
FIG. 5 is a schematic drawing showing how the degree of clearness of a blood vessel and the blood flow therein are detected by the use of a blood vessel tester according to still another preferred embodiment of the present invention.

Another embodiment of the present invention will be hereinafter described with reference to FIG. 5. Reference character $A_3$ and $B_3$ designate the junctions of the thermocouple on the surface of the bypass blood vessel 1C respectively which are connected to the measuring instrument 3C with metal wires so as to form a thermocouple.

According to this embodiment of the present invention, the degree of clearness inside the blood vessel and the blood flow rate therein may be determined by one set of a thermocouple.

Accordingly this procedure is simple.

PREFERRED EMBODIMENT OF THE INVENTION

EXAMPLE 1

A bypass blood vessel having a diameter of 4 mm was transplanted to a heart of a man and connecting the coronary artery and the aorta.

The respective junctions of two sets of copper-constantan thermocouples were fixed on two places on the surface of by bypass blood vessel which places were spaced from each other a distance of 5 cm. The terminals of the two sets of the thermocouples were fixed respectively in a thermostat which was located outside the man's body and was kept at 0° C. 24 hours after the operation of closing the said man's chest was over, 7 ml of grape sugar solution at 0° C. was transfused into the bypass blood vessel from the lower vena cava, whereby a maximum thermoelectromotive force of 25 $\mu V$ was created between the junctions and terminals of the two thermocouples, respectively, as shown in FIG. 2.

The period of time required for the cooling grape sugar solution to pass through the distance between the two junctions of the thermocouples which were fixed on the surface of the bypass blood vessel, was very short.

It was recognized from the result that the blood vessel was clear.

EXAMPLE 2

The degree of clearness in the bypass blood vessel described in Example 1 was inspected 2 weeks after the operation of closing the said man's chest over according to the same procedure as that described in Example 1, except that 10 ml of grape sugar solution at 0° C. was transfused into the bypass vessel from the vein of the arm.

The maximum thermoelectromotive force was 15 μV between the junctions and terminals of the two thermocouples, respectively.

It was recognized from the result that the blood vessel was still clear.

What is claimed is:

1. A method for determining whether or not a transplanted blood vessel inside a mammal is obstructed or contracted, in which a pair of temperature-sensitive elements are attached to the surface of said transplanted blood vessel at separate positions thereon which positions are longitudinally spaced-apart from each other in the direction of the blood flow of said transplanted blood vessel, said temperature-sensitive elements being capable of providing separate thermoelectromotive force outputs indicative of the temperature of the surface of said transplanted blood vessel at the respective positions, which comprises the steps of: transfusing a quantity of a cooling liquid into the blood that flows through said transplanted blood vessel at a location in the blood flow path upstream from said temperature-sensitive elements so that said temperature-sensitive elements thereby provide thermoelectromotive force outputs in response to the flow of the cooling liquid past said positions, each of said outputs varying with time and said two outputs being spaced-apart in time from each other; and measuring the time difference between corresponding points of said thermoelectromotive force outputs which time difference indicates whether or not said transplanted blood vessel is obstructed or contracted between said positions.

2. A method according to claim 1 in which said temperature-sensitive elements are the junctions of thermocouples, the terminals of the respective thermocouples being maintained at a fixed temperature.

3. A method according to claim 1 in which said transplanted blood vessel is a coronary bypass blood vessel in a human.

4. A method according to claim 1 in which said thermoelectromotive force outputs are applied to plates embedded inside the body of said mammal, and wherein said measuring step is performed by inserting needles through the skin of said body into electrical contact with said plates and transmitting said electrical outputs through said needles to a measuring instrument.

* * * * *